United States Patent
Plavec et al.

(10) Patent No.: US 12,403,049 B2
(45) Date of Patent: Sep. 2, 2025

(54) STORING DEVICE AND A SYSTEM FOR TRACKING ABSORPTION PRODUCTS

(71) Applicant: DUSAN PLAVEC, Ivancna Gorica (SI)

(72) Inventors: Dusan Plavec, Ivancna Gorica (SI); Melita Perko, Ivancna Gorica (SI)

(73) Assignee: DUSAN PLAVEC, Ivancna Gorica (SI)

( * ) Notice: Subject to any disclaimer, the term of this patent is extended or adjusted under 35 U.S.C. 154(b) by 470 days.

(21) Appl. No.: 17/800,531

(22) PCT Filed: Feb. 12, 2021

(86) PCT No.: PCT/SI2021/050005
§ 371 (c)(1),
(2) Date: Aug. 17, 2022

(87) PCT Pub. No.: WO2021/167537
PCT Pub. Date: Aug. 26, 2021

(65) Prior Publication Data
US 2023/0106075 A1    Apr. 6, 2023

(30) Foreign Application Priority Data

Feb. 18, 2020 (SI) .................... P-202000033

(51) Int. Cl.
| | |
|---|---|
| *A61F 13/551* | (2006.01) |
| *A61B 50/37* | (2016.01) |
| *A61B 90/00* | (2016.01) |

(52) U.S. Cl.
CPC ........ *A61F 13/55175* (2013.01); *A61B 50/37* (2016.02); *A61B 90/08* (2016.02); *A61B 2090/0803* (2016.02); *A61B 2090/0805* (2016.02); *A61B 2090/0807* (2016.02)

(58) Field of Classification Search
CPC .. A61F 13/55175; A61F 13/42; A61F 13/551; A61F 15/003; A61F 2013/424; A61B 50/37; A61B 90/08; A61B 90/98; A61B 2090/0804; A61B 2090/0805; A61B 2090/0803; A61B 2090/0807
USPC .......................................... 177/15
See application file for complete search history.

(56) References Cited

U.S. PATENT DOCUMENTS

| | | | |
|---|---|---|---|
| 5,555,965 A | 9/1996 | Mishina | |
| 5,629,498 A * | 5/1997 | Pollock | A61B 90/98 177/244 |
| 6,777,623 B2 * | 8/2004 | Ballard | G01G 23/3728 705/28 |
| 7,221,279 B2 * | 5/2007 | Nielsen | A61F 13/42 340/384.1 |
| 10,123,395 B2 * | 11/2018 | Harbers | H05B 47/16 |

(Continued)

FOREIGN PATENT DOCUMENTS

| | | |
|---|---|---|
| CN | 109662784 A | 4/2019 |
| WO | 9622510 A1 | 7/1996 |

*Primary Examiner* — Jacques M Saint Surin
(74) *Attorney, Agent, or Firm* — The Watson IP Group; Jovan N. Jovanovic

(57) ABSTRACT

The invention is referring to a storing device and a system for tracking absorption products and their use, which comprises said storing device and a verification device for tracking the use of absorption products in terms of their number and time of use, and which alerts the user about the status of the storing device and of potentially hazardous use of the absorption products.

14 Claims, 3 Drawing Sheets

(56) References Cited

U.S. PATENT DOCUMENTS

Figure 1:
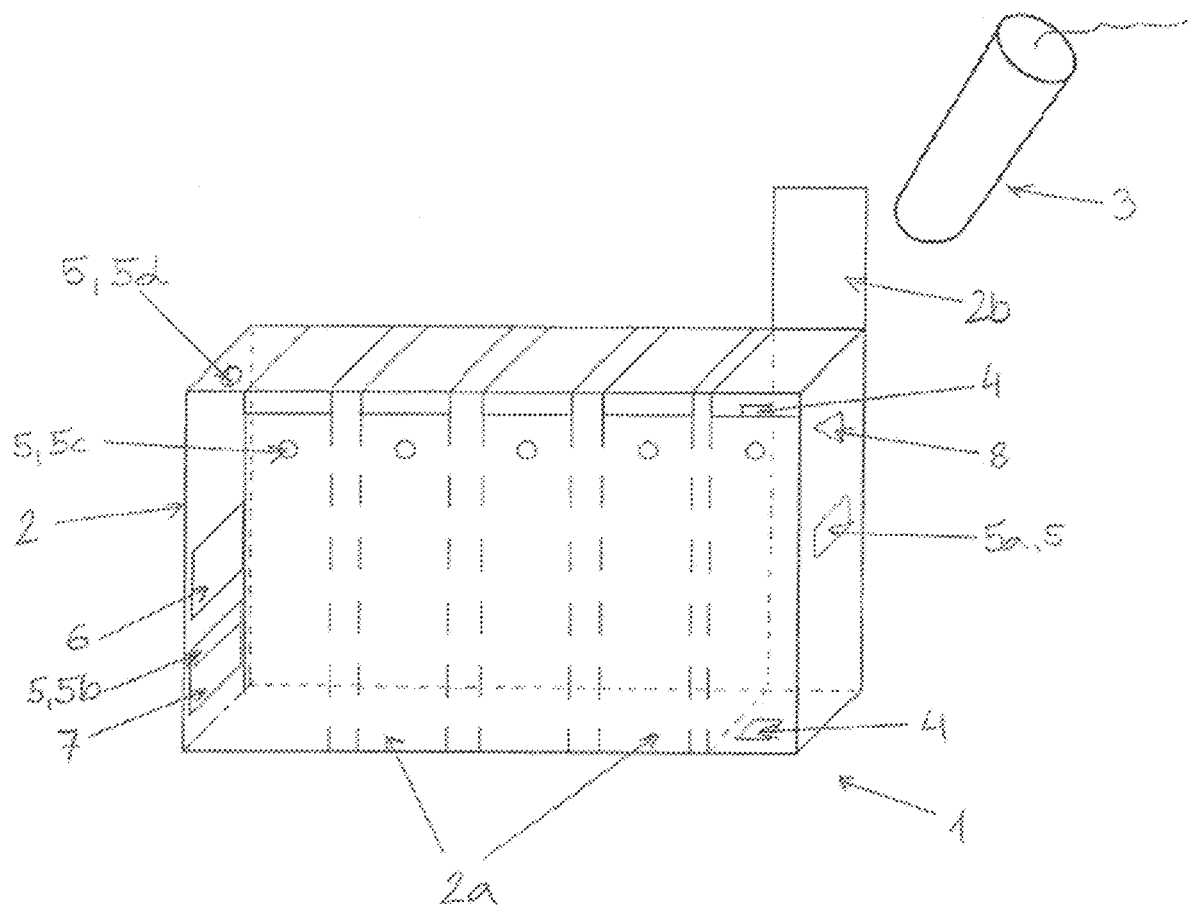

| | | | |
|---|---|---|---|
| 11,752,048 B2 * | 9/2023 | Wang | A61F 13/53713 604/369 |
| 2013/0146501 A1 | 6/2013 | Zusmanis et al. | |

* cited by examiner

STORING DEVICE AND A SYSTEM FOR TRACKING ABSORPTION PRODUCTS

The object of the invention is a storing device for absorption products and a system for tracking absorption products and their use, which comprises said storing device and a verification device for tracking the use of absorption products in terms of their number and time of use, and which alerts the user about the status of the storing device and of potentially hazardous use of the absorption products.

TECHNICAL PROBLEM

Absorption products such as tampons and surgical sponges are daily used and their misuse can result in serious health problems of the users or patients.

Tampon is a menstrual product designed to absorb blood and vaginal secretions by insertion into the vagina during menstruation. Although practical, tampons are more invasive than other menstrual products, so if not used properly they can cause health hazard, especially when a tampon is not removed in a timely fashion. For example, such situations can lead to a toxic shock syndrome which, under certain conditions, could be fatal.

Similarly, the use of surgical sponges can present great health risks if not used properly, in terms of tracking their use. For example, during a surgical operation usually many sponges are used in or on the patient's body. If one of those sponges is mistakenly left inside the patient's body, it will very likely cause severe or even fatal infections.

Therefore, there is a need for a device which can store and then track the use of tampons or surgical sponges, especially in terms of their number, time of use, duration of use and alerts the user about potentially hazardous use in a most practical way for the user.

For the purposes of this application, a term 'absorption product' will be used as a general term for both the tampons and the surgical sponges.

STATE OF THE ART

In U.S. patent application Ser. No. 14/132,733 a system for tracking surgical objects is disclosed, wherein the objects are marked with vibrantly colored stringer and tags or photo-reactive pigments to be visually detected when illuminated with the specific light source. In WO application No. 2007/044883 a tracking system is disclosed, wherein the surgical sponges are provided with machine readable information and when scanned the computer can determine if articles may be missing. In WO application No. WO 2017/095369 a feminine care absorbent article is disclosed with a color changing indicator signaling the user the appropriate time to remove or replace the article. In WO application No. WO 2018/076231 a tampon is disclosed with sensing devices with sensors and a transmission device to provide the real-time, on-line and non-invasive detection of physiological status of a female. In patent application No. CN 106264890 a diaper with a reminding function is disclosed, i.e. with the programmable controller, sensor and a buzzer, to remind the user when to replace the diaper. In patent application No. CN104287900 an absorption pad with detection means and a detachable control box to which the detection means are attached is disclosed.

All the above mentioned systems or articles require specially designed products with some kind of detecting means attached to every article in order to be able to track them in terms of their number and/or time of use and/or duration of use, which results in more complicated and more expensive production of said articles. Further, the use of articles with the attached detecting means, especially when used on the user's body may be disturbing for the user.

Figure 2:
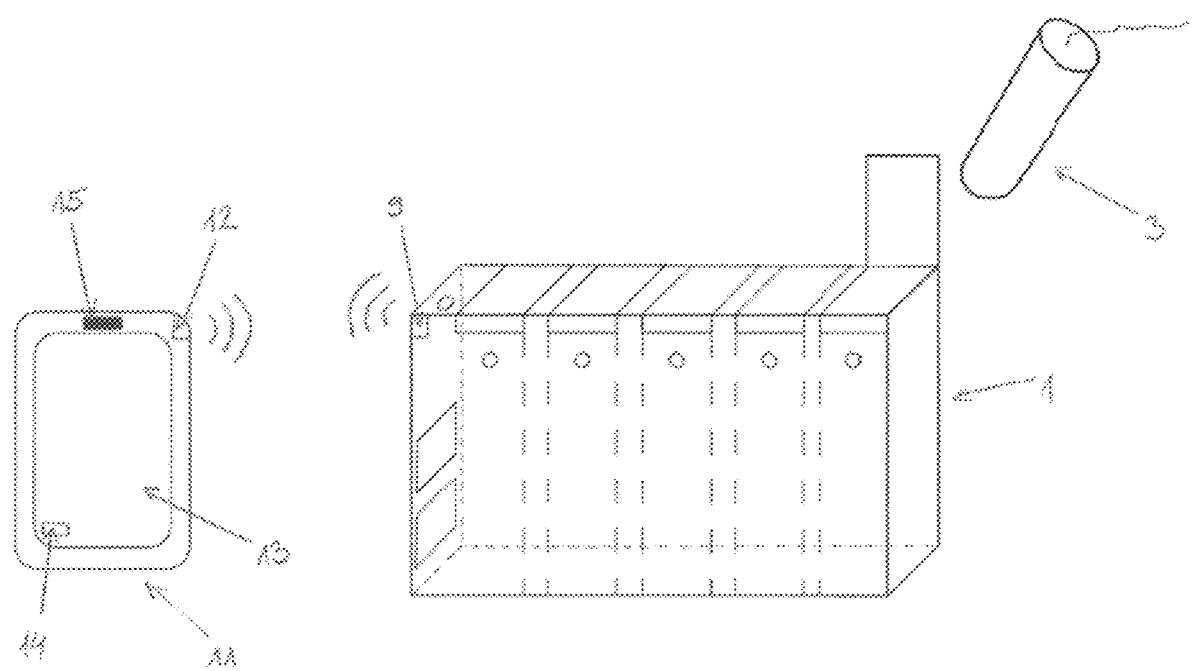
Figure 3:
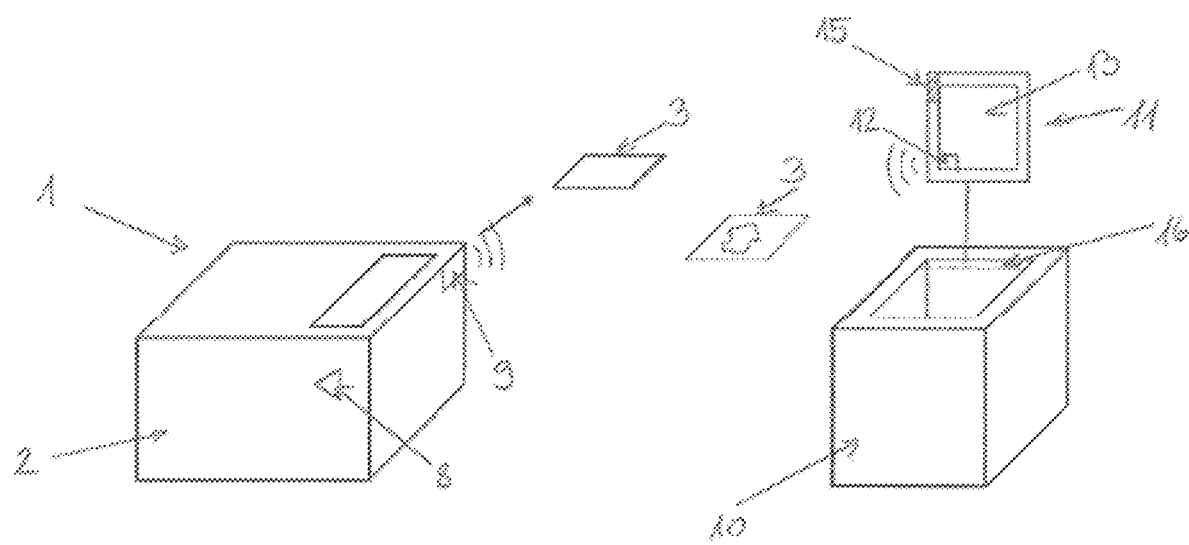

The above shortcomings are solved by the storing device and the system of the invention which will be described in more detail herein below and illustrated on the figures which show:

FIG. 1 presents an embodiment of a storing device of the invention for absorption products which are tampons FIG. 2 presents an embodiment of a system of the invention for storing and tracking the use of absorption products which are tampons FIG. 3 presents an embodiment of a system of the invention for storing and tracking the use of absorption products which are surgical sponges.

A storing system comprises a storing device 1 and a verification device 11.

A storing device 1 comprises:
- a storage compartment 2 in which absorption products 3 are stored before use;
- counting means 4 for detecting the number of absorption products 3 in the storage compartment 2 or the change thereof and for converting this information into electronically recognized signal;
- user interface means 5 for enabling the user to see the statuses of the storing device 1 and to interact with the storing device 1;
- an electronic module 6 with data processing and memory storage capabilities, wherein said electronic module 6 is configured for running software programs, for recording time, for receiving signals from the counting means 4, for receiving and sending signals to the user interface means 5, for triggering or changing statuses of the storing device 1 depending on lapsed time, signals received from the counting means 4 and from the user interface means 5, and
- a power module 7 for powering all electric components of the storing device 1.

Optionally, the storing device 1 may additionally comprise alerting means 8 for conveying more prominent alerts to the user in the near vicinity by visual, sound or haptic signals, wherein the electronic module 6 is further configured for triggering alerting means 8 on the basis of statuses of the storing device 1.

Counting means 4, user interface means 5 and alerting means 8 are connected to the electronic module 6.

The storage compartment 2 may be designed in a way to enable the absorption products 3 to remain sterile before use. For example the absorption products 3 may be stored into the storage compartment 2 of the storing device 1 immediately after their manufacturing, thus the storing device 1 is used also for transporting, distributing and delivering absorption products 3 to the final user. Therefore, the storing devices 1 may replace regular packaging for these types of products. In another embodiment, the storing device 1 may be filled with the absorption products 3 from regular packaging by the user before use, and is therefore reusable.

The storage compartment 2 may be designed in a way that the opening for the user to take out the absorption product 3 is smaller than the upper surface of the storage compartment 2, so the storage compartment 2 comprises additional pushing barrier and a flexible element inserted between the pushing barrier and the side of the storage compartment 2 which is the furthest from the opening. The pushing barrier is configured to slide from its initial position furthest away from the opening towards the opening, when absorption products 3 are taken out of the storage compartment 2. When the absorption products 3 are placed inside the storage compartment 2 during the manufacturing and packing process the flexible element is compressed. The strength and compression of the flexible element are such that the last absorption product 3 in the storage compartment 2 is pushed to the opening and thereby available to the user to be taken out. In this embodiment the position of the pushing barrier may be applied as an indication of the number of the absorption products 3 within the storage compartment 2 and the movement of the pushing barrier as an indication of the change of the number of the absorption products 3 in the storage compartment 2, so a sensor detecting the position and/or the movement of the pushing barrier may be applied as counting means 4.

In one embodiment the storage compartment 2 may be subdivided into separate sub-compartments 2a, namely one sub-compartment 2a for each absorption product 3, whereas each sub-compartment 2a has a separate lid 2b or optionally, the storage compartment 2 has one common lid.

Counting means 4 may be any type of sensor, a switch, plurality thereof or combination thereof, which can detect the number of the absorption products 3 in the storage compartment 2 or the change thereof and conveying said information with electric signal to the electronic module 6.

In the embodiment with the sub-compartments 2a, the counting means 4 is for example in a form of an electric switch connected to each of the sub-compartments 2a. The electric switch may be coupled with the lid 2b of each of the sub-compartments 2a, or placed at the bottom of each of the sub-compartments 2a, so its state is changed when the absorption product 3 is taken out of the sub-compartment 2a. In another embodiment the electric switch may be coupled with the common lid of the storage compartment 2. The electric switch records the removal of the absorption product 3 and the number of the remaining absorption products 3 in the storing device 1 is adequately updated.

In another embodiment, the counting means 4 could be implemented as a weighing sensor determining the number of absorption products 3 in the storage compartment 2 by measuring the cumulative weight of the absorption products 3 in the storage compartment 2.

The electronic module 6 most commonly includes a microchip with microprocessor, for example Arm Cortex-M4 processor, with low power consumption and accompanying electronic elements.

The alerting means 8 may be a speaker capable of producing sound alarms, one or several indicators, preferably light indicators, for example LED indicators, haptic device generating for example vibration of the storing device 1, or a combination of the aforementioned.

The user interface means 5 is designed for enabling the user to see the status of the storing device 1 and to interact with the storing device 1. In one of the embodiments the user interface means 5 may be a combination of indicators for displaying the statuses of the storing device 1 and one or more buttons 5d for enabling the user to interact with the storing device 1. For example indicators may be an indicator 5a for displaying on/off status of the storing device 1, an indicator 5b for displaying low battery status, an indicator 5c for displaying empty storage compartment 2 and/or empty individual sub-compartment 2a status, described below, or similar statuses. The indicators 5a, 5b, 5c are preferably light indicators, for example LED indicators. In one of the embodiments the user interface means 5 may display also various time values, for example, current time, time of staring the use of the absorption products or time period of the use of the absorption product. The interaction of the user with the use of buttons 5d is for example switching the storing device 1 on/off, resetting the electronic module 6, changing statuses of the storing device 1, for example stopping the alarm, or similar interactions with the storing device 1.

In another embodiment, the user interface means 5 may be a touch screen configured for both, displaying relevant information and enabling the user to interact with the storing device 1.

Preferably the power module 7 is a battery, which may be rechargeable, wherein in this case the storing device 1 additionally comprises a connector for charging the battery.

When the absorption product 3 is taken out of the storage compartment 2, counting means 4 convey this information to the electronic module 6, where a status "in use" is triggered for that particular absorption product 3. This status can be changed into other statuses either automatically by elapse of a certain time period, manually by the user through the user interface means 5 or in other ways which will be explained more in detail below. Primarily the electronic module 6 tracks the time of each absorption product 3 being in use, how many of them are in use, and optionally how many absorption products 3 are in the storage compartment 2. The electronic module 6 may optionally be configured for recording this information into its memory. Examples of other statuses may be:

"pre-use", for the absorption products 3 which are stored in the storage compartment 2, "alert", for the absorption products 3 that have been in use too long; there may be various types of alert statuses depending on various degrees of urgency. For example, for tampons the "alert" status may include a status alerting the user that the optimal time period of use is almost over, or a status that the optimal time period has expired, or a status that the maximum time period has expired.

In one embodiment, the electronic module 6 may also track if the absorption product 3, which has been used, is discarded in an appropriate way and thus tracking if the number of used absorption products 3 equals the number of the disposed absorption products 3, for example for surgical sponges which are discarded after use in a waste bin 10. In this case an additional status "safely removed and/or discarded", is triggered and additional "alert" status alerting the user that the number of the safely removed and discarded absorption products 3 differs from the number of used absorption products 3.

The alert statuses in the electronic module 6 are made visible to the user through the user interface means 5 or the electronic module 6 can additionally trigger alerting means 8, so that the user is more likely to become aware of the situations indicated by these statuses.

In addition to the storing device 1, the storing system comprises also the verification device 11, which enhances and improves the usefulness of the storing device 1 as will be described below. When a storing device 1 is used within the storing system, the storing device 1 comprises also the communication module 9 connected to the electronic module 6 and configured for communicating with a verification device 11, via known wireless networks, either short distance networks, such as Bluetooth or Wi-Fi, or long distance networks, such as telephone and data networks, for example LTE, 3G, 4G, 5G. In the latter case, the communication module 9 may for example comprise a SIM card module and a corresponding modem.

The verification device 11 with data processing and memory storage capabilities is capable of running software programs and store information, and comprises:

communication means 12 for communicating with the storing device 1 through the communication module 9 of the storing device 1;

a verification interface 13, configured for enabling the interaction of the user with the storing device 1, and optionally via the communication means 12 also with the storing device 1, and a power module 14 for powering all electric components of the verification device 11.

Optionally the verification device 11 may comprise also additional alerting means 15, for alerting the user about the said statuses. Additional alerting means 15 may be a speaker capable of producing sound alarms, one or several light indicators, for example LED indicators, haptic device generating for example vibration of the verification device 11, or a combination of the aforementioned.

Optionally the verification device 11 is configured for receiving the signal about safely discarded absorption product 3 and for informing the user accordingly. The signal about safely discarded absorption product 3 is communicated to the verification device 11 either by the user through the verification interface 13, or by other ways as described below.

In various possible embodiments the verification device 11 may be a smart phone, or a tablet or a computer with a software program (app). In the first and second example, the verification interface 13 is a touch screen and a power module 14 is a rechargeable battery integrated with the smart phone or tablet. The verification device 11 may also be integrated with or connected to the waste bin 10 into which the used absorption products 3 are safely discarded after use.

In embodiments where the verification interface 13 is a touchscreen, relevant information is presented thereon and also enables the user to operate the verification device 11 by touching the screen, and optionally enables the user to operate the storing device 1 via the communication means 12. In another embodiment the verification interface 13 may comprise one or a plurality of light indicators and a button or a series of buttons to operate the verification device 11. The verification interface 13 can be implemented also with audio devices, for example the input part of the verification interface 13 may be a microphone on a mobile phone with speech recognition software, and the output part of the verification interface 13 could be implemented as prerecorded words or sentences played on speakers on the mobile phone in accordance with the pre-loaded application software (App).

Preferably the power module 14 is a rechargeable battery.

Preferably the additional alerting means 15 is a sound producing device, for example a speaker.

The pre-loaded software on the verification device 11 or storing device 1 enables the functions of both devices, for example automatic data exchange between the storing device 1 and the verification device 11, enables the user to monitor the statuses of the storing device 1, for example the number of the absorption products 3 available in the storage compartment 2, to receive a reminder about the required refilling/purchase of new stock from the storing device 1 to the verification device 11 and the reminder to be presented on the verification interface 13, to monitor the number of used absorption products 3, to monitor the number of safely discarded absorption products 3, to set and adjust time regimes, to define the corresponding alarm statuses in relation to time regimes on the verification device 11.

First embodiment—the storing device 1 is designed to work without the need of the verification device 11, for example for storing and using absorption products 3, which are tampons—presented in FIG. 1

The storage compartment 2 in the storing device 1 is subdivided into separate sub-compartments 2a with separate lids 2b, wherein each of the sub-compartments 2a includes a tampon 3. The counting means 4 is preferably in a form of an electric switch connected to each of the sub-compartments 2a. The user interface means 5 are: an on/off indicator 5a for indicating on/off status of the storing device 1, a battery indicator 5b for indicating the battery status, sub-compartment indicator 5c on each of the sub-compartments 2a for indicating the status of the sub-compartment 2a (full/empty). These indicators are preferably light indicators, for example LED indicators. Additionally the user interface means 5 includes at least one button 5b for terminating or changing the alert status and consequently the alerting means 8. The alerting means 8 is preferably a speaker. When the user takes the tampon 3 out of the sub-compartment 2a for use, the electric switch 4 transmits the corresponding signal to the electronic module 6, which attributes the status "in use" to this particular tampon 3. This status is indicated by turning on the indicator 5c of the user interface means 5, for example by turning on the LED indicator on this particular sub-compartment 2a. The electronic module 6 simultaneously triggers also the time recording for this particular tampon 3 in use. When a pre-defined time period elapses, and no further information is transmitted to the electronic module 6, the electronic module 6 changes the "in use" status of this particular tampon 3 to the corresponding alert status. The pre-defined time period is set as an optimal time period of safe use of the tampon 3, maximum time period of safe use or it can even be defined as one of the mentioned reduced by a certain safe time period margin. The alert status in the electronic module 6 triggers the LED indicator 5c on that particular sub-compartment 2a to blink, thereby indicating the alert status to the user. As a consequence of the alert status, the electronic module 6 also triggers the speaker, as the alerting means 8, to produce a sound alarm which additionally and more prominently alerts the user about the alert status. After the user removes the tampon 3 from the body, she manually terminates the alert status and consequently the sound alarm with the user interface means 5, i.e. by pressing at least one button 5d. By pressing the button 5d, the status "safely discarded" for this particular tampon 3 is triggered in the electronic module 6 which causes the sound alarm to be terminated and the LED indicator 5c on this particular sub-compartment 2a is switched off. If the user removes and safely discards the tampon 3 before the expiration of the pre-defined time period, she also presses the button 5d and the status "in use" is changed into "safely discarded" status for this particular tampon 3 in the electronic module 6 which causes the LED indicator 5a on this particular sub-compartment 2a to be switched off.

When or if the user takes the next tampon 3 out of the sub-compartment 2a for use, the described process is initiated again.

Second embodiment—the storing system with the storing device 1 and the verification device 11, which is a smart phone, for storing and tracking the use of absorption products 3, which are tampons—presented in FIG. 2

In this embodiment the storing device 1 comprises also a communication module 9 based on Bluetooth technology to be connected with the verification device 11 through its communication means 12 based on Bluetooth technology. The verification device 11 is preferably a smart phone with a pre-loaded application software (App) that enables the smart phone to perform described functionalities according to the present invention. The verification interface 13 is a touch screen on the smart phone, and the additional alerting means 15 is a speaker on the smart phone and possibly also a vibrating device within the smart phone. The communication means 12 is the smart phone's capability of being connected with another device via Bluetooth network. When the user takes the tampon 3 out of the sub-compartment 2a for use, the electric switch 4 transmits this information to the electronic module 6, which attributes the status "in use" by switching on the LED indicator 5c of this particular sub-compartment 2a and the electronic module 6 simultaneously triggers the time recording for this particular tampon 3 in use. It is assumed that at this moment the user with her smart phone 11 is within the Bluetooth range of the storing device 1, so a corresponding signal about the status of this tampon 3 in use is sent from the storing device 1 to the smart phone 11 via communication module 9 of the storing device 1 and communication means 12 of the smart phone 11. Optionally the "in use" status can be displayed on the touch screen 13 of the smart phone 11. The smart phone, i.e. the App, also starts simultaneously to record time from when the status "in use" for this particular tampon 3 is triggered. When the pre-defined time period expires, and no further information is transmitted to the electronic module 6, the electronic module 6 changes the "in use" status of this particular tampon 3 to the corresponding alert status. Optionally, the alert status in the electronic module 6 triggers the LED indicator 5c on that particular sub-compartment 2a to blink, thereby indicating the alert status to the user. Optionally, as a consequence of the alert status, the electronic module 6 also triggers the speaker, as the alerting means 8, to produce a sound alarm which additionally and more prominently alerts the user about the alert status. After the expiration of the pre-defined time period as independently measured by the smart phone 11, and no further information is transmitted to the smart phone 11, the corresponding alert status is triggered independently also within the smart phone 11, regardless of whether at that time the smart phone 11 is within the Bluetooth range of the storing device 1. As a result, the alert status can be displayed on the touch screen 13 of the smart phone 11 and also a sound alarm or vibrating alarm is triggered by the additional alerting means 15 on the smart phone 11.

After the user removes the tampon 3 from the body and discards it safely, she manually terminates the alert status and changes it to a "safely discarded" status for this particular tampon 3 either through the touch screen 13 on the smart phone 11 or by pressing the button 5d on the storing device 1. Consequently the sound alerts and vibrating alert are terminated on the smart phone 11 and on the storing device 1, and this status is indicated in the user interface means 5 of the storing device 1, i.e. by switching off the LED indicator 5c on that particular sub-compartment 2a, and also this status change is displayed on the smart phone 11.

If any change of the statuses occurs in the smart phone 11 or the storing device 1 when the smart phone 11 is not within the Bluetooth range of the storing device 1, the statuses are synchronized immediately after the smart phone 11 is again within the Bluetooth range of the storing device 1.

If in a similar embodiment the communication module 9 is based on a long range communication network, such as LTE, instead of a short term communication network, such as Bluetooth, and correspondingly also the communication means 12 of the verification device 11, the latter will almost always be within the communication range of the storing device 1, so the synchronization of statuses between the storing device 1 and the verification device 11 may be achieved in a continuous and instant way.

If the user removes and safely discards the tampon 3 before the expiration of the pre-defined time period, she also manually terminates the "in use" status and changes it to a "safely discarded" status for this particular tampon 3 either through the touch screen 13 on the smart phone 11 or by pressing the button 5d on the storing device 1.

The storing system is even more practical for the user then the storing device 1 as a standalone device, because it is more likely that the user will have smart phone 11 with her so she will notice the alert status and other statuses on the smart phone 11 than, that she will be within hearing or seeing distance from the storing device 1 to notice the sound alarm, alert status or other statuses as displayed by the user interface means 5, for example the blinking LED indicator 5c. Also, the user having the smart phone 11 with her will be able to interact with the storing device 1 regardless of whether she is in a close proximity of the storing device 1.

Third embodiment—the storing system with the storing device 1 and the verification device 11 for storing and tracking the use of absorption products 3, which are surgical sponges—presented in FIG. 3

In this embodiment the storing system is particularly adapted to be used with absorption products 3 that are surgical sponges within a context of medical operation, where all sponges must be accounted for, especially before the end of the operation. The storing device 1 additionally comprises a communication module 9 based on standard Bluetooth technology to be connected with the verification device 11 through its communication means 12 based on Bluetooth technology. The verification device 11 is preferably a tablet with a pre-loaded application software (App) that enables the tablet to perform described functionalities according to the present invention. The verification interface 13 is a touch screen on the tablet, and the additional alerting means 15 is a speaker on the tablet and possibly also a vibrating device within the tablet.

When the user takes the surgical sponge 3 from the storing compartment 2, the counting means 4, which is in this embodiment preferably a weighing sensor, transmits the signal about this information to the electronic module 6 which attributes the status "in use" for this particular sponge 3 and the electronic module 6 simultaneously triggers the time recording for this particular sponge 3 in use. This status and other subsequent statuses and changes thereof within the storing device 1 are sent to the verification device 11 through a Bluetooth network, and vice versa. Optionally, the verification device 11 independently tracks the time of the statuses for each particular sponge 3. When a particular sponge 3 is discarded into a waste bin 10, this information is detected by the verification device 11 either by the user manually through the touch screen 13 of the tablet or automatically by the detection means 16 able to detect the number of the sponges 3 in the waste bin 10 or the change of that number. When the information about the discarded sponge 3 is received by the system, the corresponding status of that particular sponge 3 is changed from "in use" into status "safely discarded". The storing system continuously compares the statuses of the sponges 3, i.e. compares the number of surgical sponges 3 taken from the storage compartment 2 with the number of surgical sponges 3 discarded into the waste bin 10. The discrepancy between these two numbers shows how many sponges 3 are in use, so the information about the discrepancy or the number of sponges 3 in use is shown on the user interface means 5, the verification interface 13 or both. Optionally, the system may be programmed that after a pre-defined time period, for example the estimated time duration of the medical operation, the number of sponges 3 in use is still more than zero, the storage device 1 or the verification device 11 triggers the corresponding alert status, which in turn triggers the additional alerting means 15 or optional alerting means 8 on the storing device 1, thereby more prominently alerting the user about the potentially missing sponges 3. In this way the user can always track the number of sponges 3 in use as well as check if all surgical sponges 3 used during the medical operation have been safely discarded.

The mentioned detection means 16 may be a suitable sensor configured for automatically detecting each individual surgical sponge 3 when placed into the bin 10 or a button with which the user manually indicates when each individual surgical sponge 3 is placed into the bin 10.

The invention claimed is:

1. A personal storing device for tampons configured for storing and tracking the use of each individual tampon, wherein said device comprises:
    a storage compartment in which tampons are stored before use;
    a counting means for detecting the number of tampons in the storage compartment or for detecting a change in the number of tampons in the storage compartment, wherein the counting means is configured to convert this information into electronically recognized signals;
    a user interface means for enabling the user to see a status of the storing device and to interact with the storing device;
    an electronic module with data processing and memory storage capabilities, wherein said electronic module is configured for running software programs, recording time, receiving signals from the counting means, receiving and sending signals to the user interface means, and triggering or changing the status of the storing device depending on lapsed time, signals received from the counting means and from signals received from the user interface means, wherein the storage device has at least three statuses capable of being recognized by the electronic module and user interface means; and
    a power module for powering all electric components of the storing device and wherein the counting means and the user interface means are connected to the electronic module.

2. The personal storing device according to claim 1, wherein the storage compartment is subdivided into separate sub-compartments, with each sub-compartment corresponding to a tampon product.

3. The personal storing device according to claim 1, wherein the counting means is a weight sensor configured to determine the number of tampons in the storage compartment by measuring the cumulative weight of the tampons in the storage compartment.

4. The personal storing device according to claim 2, wherein the counting means is an electric switch connected to each of the sub-compartments, wherein the electric switch is coupled with a lid of each sub-compartment or placed at a bottom of each of the sub-compartment, or wherein the electric switch is coupled with a common lid of the storage compartment.

5. The personal storing device according to claim 1, wherein the user interface means is a combination of an indicator for displaying at least an on/off status of the storing device 1, an indicator for displaying a low battery status of the storing device, an indicator for displaying an empty storage compartment status of the storing device, and one or more buttons for enabling the user to interact with the storage device by switching the storing device on/off, by resetting the electronic module, and by changing the status or statuses of the storing device.

6. The personal storing device according to claim 5, wherein the indicators are light indicators, for example LED indicators.

7. The personal storing device according to claim 1, wherein the storing device additionally comprises an alerting means, connected to the electronic module, for conveying prominent alerts to the user by visual, sound, or haptic signals and wherein the electronic module is further configured for triggering the alerting means on the basis of statuses of the storing device.

8. The personal storing device according to claim 7, wherein the alerting means is at least one of a speaker capable of producing sound alarms, a light indicator or series of light indicators, or a haptic device for generating vibration of the storing device.

9. A personal storing system for tracking tampons, wherein said storing system comprises a storing device according to claim 1 and a verification device with data processing and memory storage capabilities, configured for running software programs and store information, wherein the storing device also comprises a communication module connected to the electronic module and configured for communicating with the verification device via wireless networks, and wherein said verification device comprises:
    a communication means for communicating with the storing device through the communication module of the storing device;
    a verification interface, configured for enabling the interaction of the user with the storing device, and optionally via the communication means also with the storing device, and
    a power module for powering all electric components of the verification device.

10. The storing system according to claim 9, wherein the verification device additionally comprises additional alerting means, for alerting the user about the statuses of the storing device.

11. The personal storing system according to claim 9, wherein the verification device is a smart phone, or a tablet or a computer.

12. The personal storing system according to claim 9, wherein the verification interface is a touch screen and a power module is a rechargeable battery integrated with the smart phone or tablet.

13. The personal storing system according to claim 9, wherein the verification interface is implemented with audio devices, wherein the audio devices comprise a microphone on a mobile phone with speech recognition software, and a speaker of the mobile phone to play prerecorded words or sentences in accordance with the pre-loaded application software.

14. A method of using the device of claim 1, wherein the method comprises the following steps:
    a user takes a tampon out of the storage compartment for use;
    the electric switch transmits a corresponding signal to the electronic module, which attributes an "in use" status to this particular tampon and wherein said status is indicated to the user by turning on the indicator of the user interface means;

the electronic module is simultaneously triggers the time recording for this particular tampon;

after elapsing of pre-defined time period, the electronic module changes the "in use" status of this particular tampon to the appropriate alert status, which triggers the indicator on the storage compartment to blink, thereby indicating the alert status to the user;

the electronic module simultaneously triggers the alerting means to produce a sound alarm which further alerts the user about the alert status;

the user removes the tampon from the body and manually terminates the alert status and sound alarm;

by terminating the alert status, the "safely discarded" status for this particular tampon is triggered by the electronic module, causing the sound alarm to be terminated and the indicator on the storage compartment to be switched off.

* * * * *